United States Patent [19]

Marciel

[11] Patent Number: Plant 7,562

[45] Date of Patent: Jun. 18, 1991

[54] ROSE PLANT NAMED DEVCALI

[75] Inventor: Stanley G. Marciel, Aptos, Calif.

[73] Assignee: DeVor Nurseries, Inc., Watsonville, Calif.

[21] Appl. No.: 452,111

[22] Filed: Dec. 18, 1989

[51] Int. Cl.[5] ..... A01H 5/00

[52] U.S. Cl. ..... Plt./20

[58] Field of Search ..... Plt./28, 29, 19, 20, Plt./21

*Primary Examiner*—Howard J. Locker

*Attorney, Agent, or Firm*—Charles W. Rummler

[57] ABSTRACT

A new and distinct greenhouse rose distinguished by its tryian purple flowers of medium size borne singly on strong upright stems of medium length growing from a vigorous free branching bush of about medium size with a height of about 26 inches and particularly suited to pot plant culture, the flowers having a long lasting quality of several weeks both on the plant and as a cut flower.

1 Drawing Sheet

BACKGROUND OF THE NEW PLANT

This new rose variety originated as a seedling of a hybrid produced by me at Pleasanton, Calif. by my crossing a pair of unnamed varieties selected from a collection of plants maintained by me for breeding purposes this crossing being done with the object of producing a new red flowering plant for pot plant culture. This particular seedling was selected for propagation because of its profuse production of purple red blossoms of medium size carried on strong upright stems of a plant having a height of about 26 in. and abundant foliage and I propagated this plant by budding at Pleasanton, Calif with very satisfactory results. This propagation was carried on through several successive generations which thereby conclusively determined that its novel characteristics would hold true from generation to generation and appeared to be firmly fixed.

DESCRIPTION OF THE DRAWING

My new rose plant is illustrated by the accompanying photographic drawing which shows several blooms, some foliage and a bud, the colors shown being as nearly true to those herein specified as is reasonably possible to obtain by conventional photographic procedures.

DESCRIPTION OF THE NEW VARIETY

The following is a detailed description of my new rose plant based upon observation of plants grown in greenhouse at Pleasanton, Calif., with the color designations being according to The R.H.S. Colour Chart published by The Royal Horticultural Society of London, England.

THE PLANT

Origin: Seedling.

Parentage: Unnamed and unpatented varieties selected from plants maintained in greenhouse at Pleasanton for breeding purposes.

Classification: Greenhouse Rose.

Form: Upright free branching bush.

Growth: Vigorous and sturdy.

Height: About 158 cm.

Main stem length: About 26 in. (67 cm.) from last flower cut.

Flowering stem length: About 50 cm.

Foliage:

- *Quantity.*—Abundant.
- *Number of leaves.*—5 or 6, From last flower cut.
- *Shape of leaf.*—Odd pinnate.
- *Size.*—Averages about 13 cm. long and about 9 cm. wide for 7 leaflet leaf.
- *Leaflets.*—Number: 5 or 7. Size: Average about 62 mm. long and about 37 mm. wide. Shape: Generally elliptic with acute apex and serrated margins. Texture: Leathery. Aspect: Smooth. Color: Upper side — 137B. Under side — 191B.
- *Stipules.*—Hairy adnate.
- *Rachis.*—5 leaf, 85 mm. long; 7 leaf, 110 mm. long.

Thorns:

- *Size.*—About 8 mm. long.
- *Color.*—152-D.

THE BUD

Character: Good commercial shape shortly after sepals divide and spread outwardly.

Size: About 38 mm. long and 30–35 mm. wide.

Color of petals: Red purple, 57-A.

Sepals:

- *Number.*—Five.
- *Character.*—Branching with small leafs below one side. The sepals stand up when the flower opens.
- *Color.*—Inside — 147-D. Outside — 144-A.

Calyx:

- *Shape.*—Funnel-shaped.
- *Size.*—Medium.
- *Splitting.*—Calyx does not split.
- *Aspect.*—Smooth.

Flower stem:

- *Length.*—About 50 cm.
- *Character.*—Slender and erect.
- *Color.*—144-C.

THE FLOWER

Blooming habit: Continuous and profusely, blooming freely under greenhouse conditions through all seasons.

Size of bloom: Medium.

- *Diameter.*—About 55 to 60 mm.
- *Depth.*—About 40 mm.

Borne: Singly on strong upright stems.

Shape:

*When bloom first opens.*—High center.
*When bloom matures.*—Nicely imbricated.

Petalage:
*Number.*—22.
*Arrangement.*—Imbricated.
*Form.*—Cordate with ruffled outwardly curved margins and an acuminate apex.
*Texture.*—Soft.
*Appearance.*—Velvety.
*Color.*—The closest is red purple, 57-A. The outer petal body having a little more purple and a base of yellow, 4-C. The inside petals having a body color of deeper red.

Petaloids:
*Number.*—3.
*Size.*—About 28 mm. long and 24 mm. wide.
*Color.*—57-A, but with a slightly deeper red and a base color of 8-C.

Flower stem:
*Length.*—About 50 cm.
*Color.*—144-C.
*Character.*—Sturdy and upright.

Discoloration after full bloom: Slight discoloration.
Persistence: The flower petals hang on and dry.
Fragrance: Slight.
Disease resistance: Moderately resistant to mildew, rust, and black spot as observed at Pleasanton, Calif.
Lasting quality: Long-lasting both on plant and as cut flower.

THE REPRODUCTIVE ORGANS

Stamens:
*Number.*—107.
*Arrangement.*—Introse.
*Anthers.*—Size: 3 mm. Color: Greyed orange, 163-C.
*Filaments.*—Length: About 8 mm. Color: 2-D.
*Pollen.*—Color: Greyed orange, 163-C.

Pistils:
*Number.*—72.
*Styles.*—Length: 12 mm. Color: Greyed purple, 186-A.
*Stigmas.*—Color: Greyed orange, 163-D.

Character of the ovaries: Long, slender, slightly flattened with a covering of silvery hairs.

THE FRUIT

Fertility: The fruit is fertile.
Shape: Round.
Color: Orange, 24-A.

I claim:

1. The new and distinct variety of greenhouse rose plant substantially as herein shown and described, characterized in particular by its continuous and profuse production of near tyrian purple flowers of medium size carried on strong upright stems, its free branching growth habit and its abundant production of foliage.

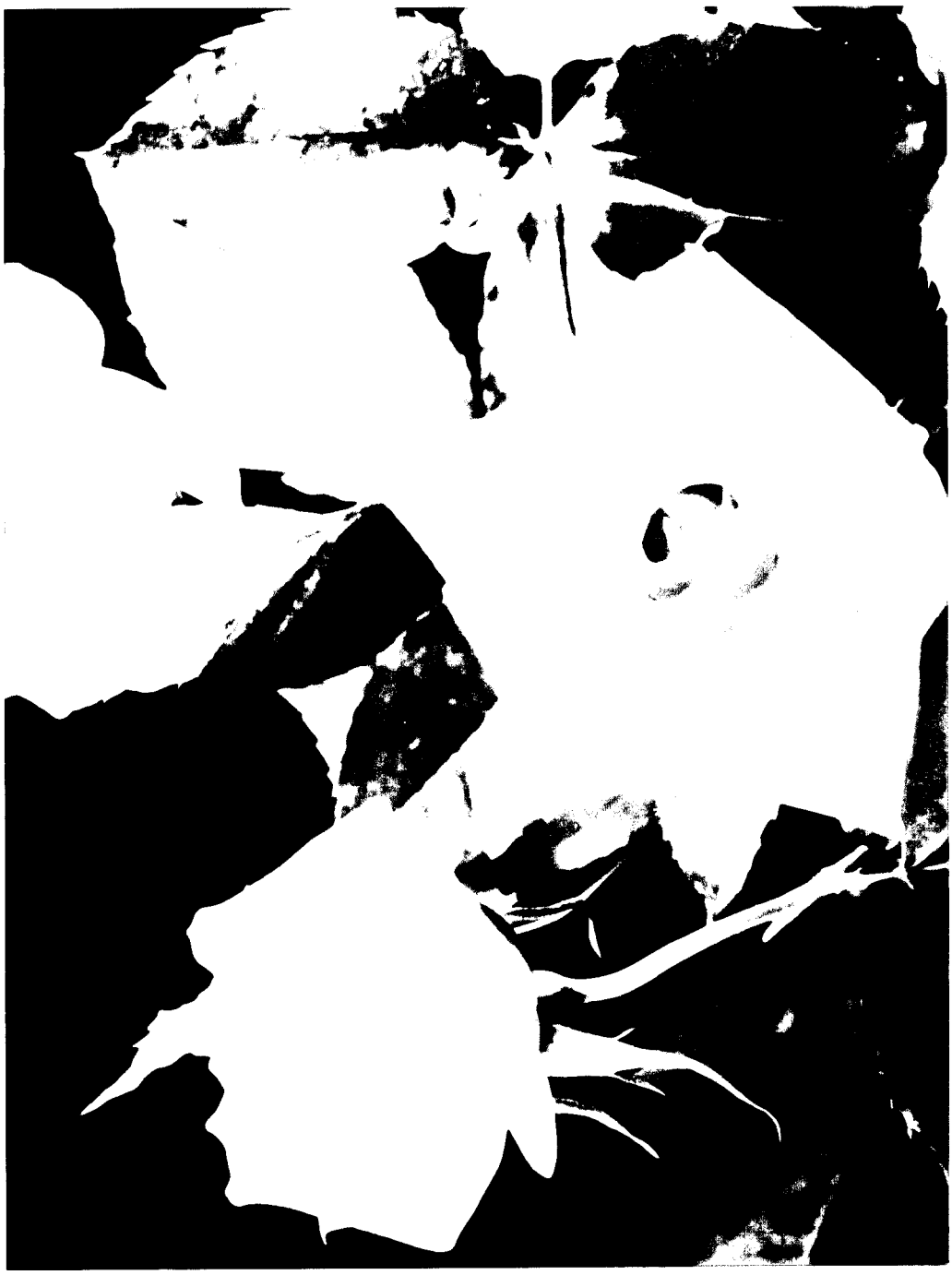

* * * * *